US007291741B2

(12) United States Patent
Križanovič et al.

(10) Patent No.: US 7,291,741 B2
(45) Date of Patent: Nov. 6, 2007

(54) PROCESS OF PRODUCTION OF N-ALKYL-2-BENZTHIAZOLYSULFENEIMIDES, DEVICE FOR THEIR PRODUCTION AND METHOD OF THEIR PURIFICATION

(75) Inventors: Karol Križanovič, Svätý Jur (SK); Gabriel Šereda, Bratislava (SK); Alžbeta Štrauchová, Bratislava (SK); Jozef Pintér, Nitra (SK); Kamil Vali, Tvrdošovce (SK)

(73) Assignee: Duslo A.S., Sal'a (SK)

( * ) Notice: Subject to any disclaimer, the term of this patent is extended or adjusted under 35 U.S.C. 154(b) by 501 days.

(21) Appl. No.: 10/486,294

(22) PCT Filed: Apr. 25, 2002

(86) PCT No.: PCT/SK02/00006

§ 371 (c)(1),
(2), (4) Date: Mar. 15, 2004

(87) PCT Pub. No.: WO03/014096

PCT Pub. Date: Feb. 20, 2003

(65) Prior Publication Data
US 2004/0210062 A1  Oct. 21, 2004

(30) Foreign Application Priority Data
Aug. 10, 2001 (SK) ................... 1153-2001

(51) Int. Cl.
*C07D 277/80* (2006.01)
(52) U.S. Cl. .................................... 548/158
(58) Field of Classification Search .............. 548/158
See application file for complete search history.

(56) References Cited

U.S. PATENT DOCUMENTS

| 2,257,974 A | 10/1941 | Messer | 260/306 |
|---|---|---|---|
| 2,304,557 A | 12/1942 | Ebelke | 260/304 |
| 2,321,305 A | 6/1943 | Messer | 260/788 |
| 2,321,306 A | 6/1943 | Messer | 260/306.6 |
| 2,860,142 A | 11/1958 | Couly | 260/306.6 |
| 2,873,277 A | 2/1959 | Sundholm | 260/306.6 |
| 2,889,331 A | 6/1959 | Sundholm | 260/306.6 |
| 2,962,481 A * | 11/1960 | Kerrigan et al. | 525/349 |
| 3,875,177 A | 4/1975 | Maison | 260/306.6 |
| 5,204,481 A | 4/1993 | Carroll et al. | 548/157 |
| 5,286,870 A | 2/1994 | Sicheneder | 548/157 |
| 5,436,346 A | 7/1995 | Eisenhuth et al. | 548/168 |
| 5,684,346 A | 11/1997 | Mickos et al. | 310/58 |
| 5,840,908 A | 11/1998 | Singh et al. | 548/104 |
| 6,306,860 B1 | 10/2001 | Yoon et al. | 514/253.13 |

FOREIGN PATENT DOCUMENTS

| GB | 817039 | 7/1959 |
| SU | 478011 | 7/1975 |
| WO | WO92/05218 | 4/1992 |

OTHER PUBLICATIONS

N.K. Sundholm, Ind. Eng: Chem. 53, No. 3, 239-240 Mar. 1960.
Abstract of EP 721 946 Jul. 17, 1996.
PCT Search Report for PCT SK/02/00006.

* cited by examiner

*Primary Examiner*—Rebecca Anderson
(74) *Attorney, Agent, or Firm*—Ohlandt, Greeley, Ruggiero & Perle, LLP; George W. Rauchfuss, Jr.

(57) ABSTRACT

The solution concerns a process of production of N-alkyl-2-benzthiazolylsulfeneimides by means of a reaction of 2-benzthiazolylsulfenyl chloride with an excess of a corresponding alkylamine in an anhydrous reaction medium. Removement of water and moisture from the reaction medium is ensured by azeotropic distillation of a part of the solvent. The method solves also trapping of the excess amine by extraction with water to recycle it in the process, removing of the unconverted raw material from the crude product by chemical refining with aqueous lye and extraction of by-products and pitches by elutriating the product in an organic solvent with the aim to obtain pure benzthiazolylsulfeneimide containing no less than 95% of the active substance, which can be used as a vulcanization accelerator in rubber mixtures. A device for performing this method consists of a reactor with a multiple propeller mixer on a common shaft

15 Claims, 1 Drawing Sheet

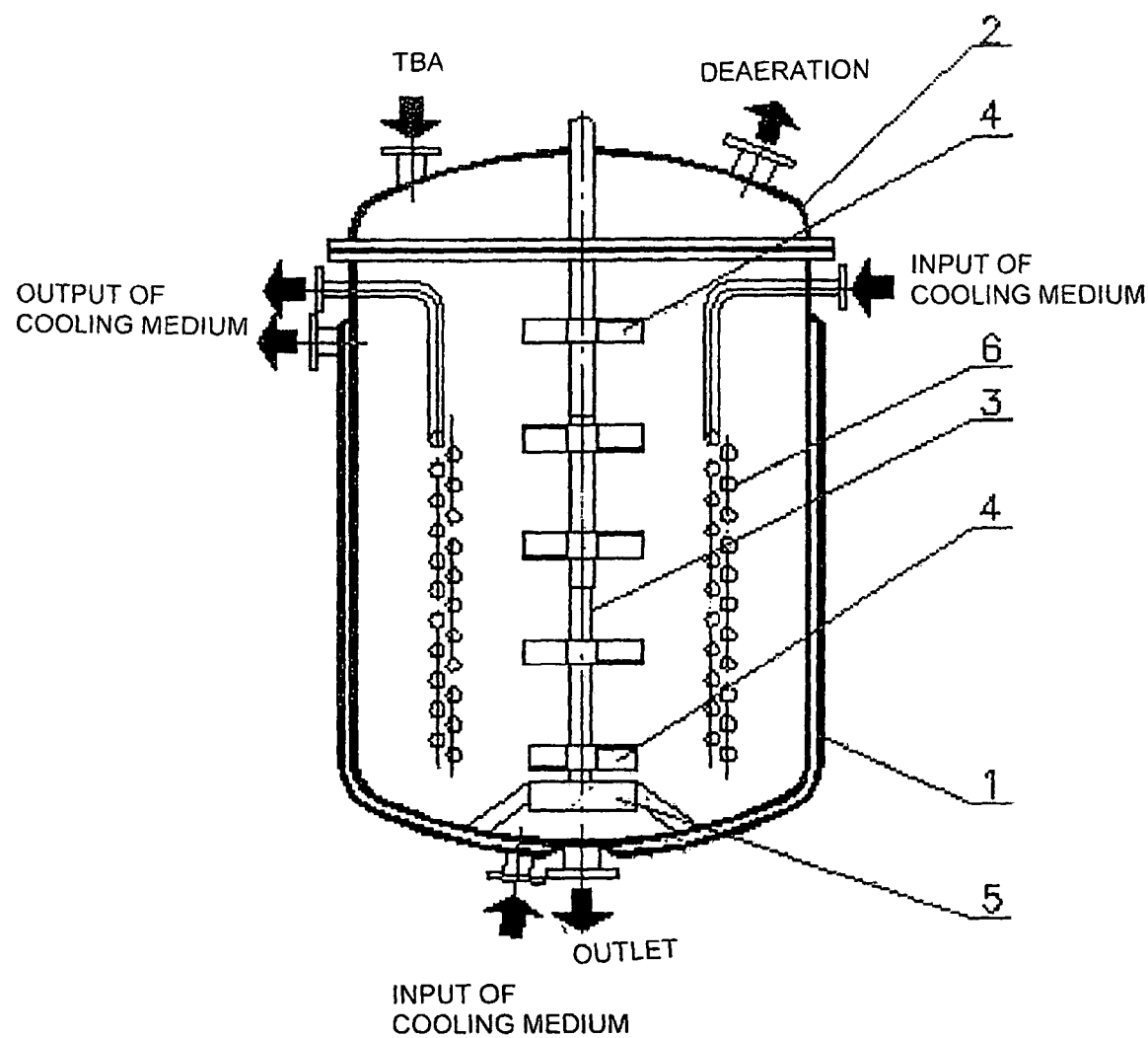

PROCESS OF PRODUCTION OF N-ALKYL-2-BENZTHIAZOLYSULFENEIMIDES, DEVICE FOR THEIR PRODUCTION AND METHOD OF THEIR PURIFICATION

This application is a 371 of PCT/SK02/00006 filed Apr. 25, 2002.

TECHNICAL FIELD

The invention concerns an improved method of production of N-alkyl-2-benzthiazolylsulfeneimides as well as an equipment for their production and a method of their purification.

BACKGROUND ART

Bis-benzthiazolyl-alkyl-sulfeneimides which are represented by a general formula (I)

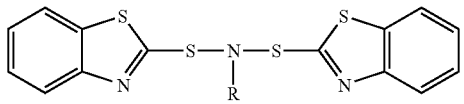

where R is a $C_1$ to $C_{12}$ unbranched or branched alkyl, $C_3$ to $C_9$ cycloalkyl or a substituted or unsubstituted aryl group, are known for very long and they are used in the rubber industry as promising vulcanisation accelerators which provide for excellent operational safety of rubber mixtures, impart better resistance against reversion to the vulcanizates and better physical properties at prevulcanization at higher temperatures, and which have excellent storage stability. Sulfeneimides, based on primary amines, do not form stable N-nitrosoamines and, therefore, they are predetermined as suitable substitutes for hygienically?? problematic sulfeneamide derivatives of secondary amines (for example, N-oxydiethylene-2-benzthiazolyl-sulfeneamide) having comparable scorching times and vulcanization times.

Examples of known sulfeneimide accelerators are N-cyclohexyl-2-benzthiazolyl-sulfeneimide (CBSI), N-tert-butyl-2-benzthiazolylsulfeneimide (TBSI), N-isopropyl-2-benz-thiazolylsulfeneimide as well as N-tert-octyl-2-benzthiazolylsulfeneimide. The chlorinating method of sulfeneimide preparation is started from 2-benzthiazolylsulfenyl chloride, the preparation of which (described in the U.S. Pat. No. 2,257,974) consists from chlorination of 2,2'-di-benzthiazolyldisulfide (MBTS) in a nonreactive organic solvent with chlorine. The U.S. Pat. No. 2,304,557 in the name of Ebelke solves the sulfenyl chloride preparation from 2-mercaptobenzthiazole (2-MBT) in nonreactive solvents, such as $CCl_4$, at reflux, or in the case of solvents which are attacked by chlorine, such as benzene, at a lower temperature. After the chlorination has been completed, the mixture is heated to boiling point with the aim to release the excessive halogen and the resulting HCl. The prepared benzthiazolylsulfenyl chloride is sensitive to atmospheric moisture.

The second step of the above given preparation of sulfeneimides is a reaction of the intermediate—sulfenyl chloride—with a primary amine in the presence of a suitable base, which may be constituted by the primary amine itself.

The U.S. Pat. Nos. 2,321,305 and 2,321,306 in the name of Messer concern preparation of bis- and tris-sulfeneamides by inverse dosing of sulfenyl chloride into the present amine in an organic solvent. The amine hydrochloride is filtered off and the product is obtained by evaporating solvent from the filtrate.

In the GB patent No. 817,039 Kerrigan presents preparation of a new accelerator, N-tert-octyl-2-benzthiazolylsulfeneimide, at 20 to 40° C., where the system temperature is increasing by the heat of reaction. In order to trap HCl, either an excess of amine or scavengers, such as pyridine, triethylamine and the like, are used. After the reaction is completed, the mixture is cooled down, hydrochloride is filtered off and the mixture is successively washed with water, 5% acetic acid, 5% NaOH, water, and it is finish dried over $Na_2SO_4$. The solvent $CCl_4$ is removed by distillation at a reduced pressure and the crude product is recrystallized from petroleum ether.

The U.S. Pat. Nos. 2,873,277 and 2,889,331 in the name of Sundholm concern the preparation of N-alkyl- a N-cycloalkyl-bis(2-benzthiazolylsulfene)amides (TBSI, CBSI and the like) by a reaction of the corresponding amine with sulfenyl chloride at a mole ratio of 3:2 and at a temperature in the range of −40 to +50° C.; the dosing method (concurrent, inverse or direct) influences quality of the product. After the reaction is completed, amine hydrochloride is filtered off, the product is obtained by evaporating solvent from the filtrate, and it may be recrystallized from ligroin.

N. K. Sundholm (Ind. Eng. Chem. 52, 239, 1960) states that the product quality is improved by lower reaction temperatures (−10° C. and lower) and by quick direct dosing. If adding inversely a small amount of sulfenyl chloride into the reactive amine, the reaction may develop in the direction to monosulfeneamide, where neither a temperature lowering to −20° C. will help.

The U.S. Pat. No. 478,010 in the name of Chitrina et al. concerns a method, how to obtain N-cyclohexane-dienyl-1,4-bis-(2-benzthiazolyl)-sulfeneamide by direct dosing of unsaturated 1,4-cyclohexanedienylamine into sulfenyl chloride at a molar ratio of 2:1 at a temperature of −15 to −5° C. with a subsequent increase of temperature to 25 to 30° C. in the presence of a tertiary amine as an HCl scavenger.

In the above mentioned patent publications about sulfeneimide preparation by a chlorinating method, it is required to use dry or anhydrous solvents, respectively. Alternative methods of production of N-alkyl- and N-cycloalkyl-2-benzthiazolylsulfeneimides from the corresponding monosulfeneamides by means of a reaction with organic anhydrides are described in the U.S. Pat. Nos. 2,860,142, 3,875,177 and 5,840,908, and by means of a reaction with strong mineral acids in anhydrous hydrocarbon medium in WO 92/05218, WO 99 58526 and EP 0 574 369.

In EP 0 529 449, Sicheneder describes a promising process of preparation of bis-benzthiazolyl-alkylsulfeneimides, such as TBSI, by a reaction of alkylamines (without proton at the α-carbon) with a substituted 2-MBT in the presence of oxygen or oxygen containing gas, copper or copper compounds as a catalyst in an inert organic solvent.

Although in the older references, concerning this problem, these compounds are termed bis(sulfeneamides), it is chemically more correct to term them sulfeneimides.

The object of the method according to the present invention is to eliminate the necessity of removing the amine hydrochloride by filtration, crystallization from petroleum ether, as well as to obtain the final product of better quality and with higher yield.

DISCLOSURE OF INVENTION

The above given object can be achieved by a method of production of N-alkyl-2-benthiazolyl-sulfeneimides of the general formula I

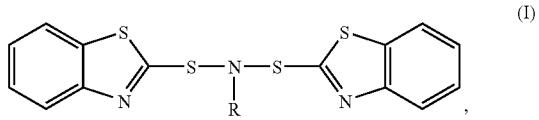

where R is a $C_1$ to $C_{12}$ unbranched or branched alkyl, $C_3$ to $C_9$ cycloalkyl, by means of a reaction of 2-benzthiazolylsulfenyl chloride, an intermediate prepared from 2,2'-dibenzthiazolyl disulfide or 2-mercaptobenzthiazole using chlorine in the presence of an inert solvent, with an excess of a corresponding alkylamine in an inert reaction medium, according to the present invention. The nature of the invention consists in that the reaction with sulfenyl chloride is performed using a 10 to 100% excess of the concentrated alkylamine, compared with the theoretical amount, i. e. 3.3 to 6 equivalents of alkylamine per 2 equivalents of sulfenyl chloride as required by theory, and moisture of the solvent, raw material, equipment as well as the residue of not isolated alkylamine are removed by azeotropic distillation of a part (15% at most) of the solvent, possibly at a reduced pressure. The primary amine which is present in an excess serves mutually as a scavenger for the arising acid.

The free amine together with alkylammonium chloride from the reaction mixture are trapped by extraction using water or diluted acid, respectively, and by gravitational phase separation, from which amine is regenerated by distillation after a reaction with aqueous NaOH.

Condensation of benzthiazolylsulfenyl chloride with alkylamine is a heterogeneous reaction accompanied with reaction heat generation, and therefore, an important part of the process is an equipment which allows intensive mixing and conducting the reaction heat away during condensation. It is preferred to perform it in an equipment according to the present invention, the nature of which consists in that it comprises a reactor with multiple propeller mixers on a common shaft. The reactor consists of a vessel in which propeller mixers are arranged on a common shaft, and of a lid. Individual levels?? of the propeller mixers are oriented opposite one another. The shaft is supported at the bottom bearing. A cooling coil is arranged in the reactor. In this way the required intensive mixing and cooling in the decisive technological node is ensured.

The solvent (a part of it or as a whole) is removed from the reaction system by azeotropic distillation with water at a reduced pressure and at a temperature not greater than 50° C. In order to remove the disulfide which has not reacted, aqueous sodium hydroxide is added at a temperature of 20 to 50° C. Chemical refining by the lye is performed before or during thickening the reaction mixture, and the sulfeneimide is separated from the solution containing impurities by filtration. The crude (not purified) product itself can already be used as a rubber accelerator.

The invention further concerns a method of purification of the crude product N-alkyl-2-benzthiazolylsulfeneimide, the nature of which consists in that the crude product is elutriated at a temperature of 10 to 50° C. during 0.5 to 2 h in a polar organic solvent, selected from a group comprising acetone, isopropanol, ethanol, their mixtures or possibly azeotropic mixtures with water, and the pure, insoluble sulfeneimide is separated from the solution which contains dissolved impurities by filtration.

Alternatively, aqueous suspension of the crude product is mixed at a temperature of 10 to 50° C. during 0.5 to 2 h in a nonpolar organic solvent, selected from a group comprising alkanes, cycloalkanes, aromates and their mixtures, and the pure, insoluble sulfeneimide is separated from the aqueous-organic emulsion which contains dissolved impurities by filtration.

After the solvent has been evaporated, the crude product is not crystallized from nonpolar solvents as before, but it is refined with an aqueous lye, while the by-products of the reaction are extracted with a suitable organic solvent which may consists of the solvent used in the process. There are certain cases, where it is possible to omit completely the chemical refining by a lye, and to refine the crude sulfeneimide by mixing it in a polar organic solvent, preferably in alcohol or acetone.

The advantage of the method according to the present invention consists in that, contrary to present procedures, the amine hydrochloride is not removed from the thus prepared reaction mixture by filtration, but it is washed out with water. The crude product need not to be crystallized from petroleum ether, and moreover, the method according to the present invention leads to better quality and to higher yield of sulfeneimide.

BRIEF DESCRIPTION OF DRAWINGS

The equipment according to the present invention is shown in detail in the attached FIGURE.

EXAMPLES OF EMBODIMENTS

The following examples explain the invention in more detail, but they do not limit the scope of the invention.

Example 1

Preparation of
N-tert-butyl-2-benzthiazolylsulfeneimide (TBSI) in toluene

Chlorination of 2,2'-dibenzthiazolyl disulfide:

60.0 g (0.1742 mol) of 2,2'-dibenzthiazolyldisulfide (commercially available Altax containing 96.51% of the active substance according to HPLC) and 750 ml of toluene were added to a 2 l three-necked flask. 75 ml of the solvent were distilled off under stirring, and the solution was cooled down to 25° C. Dry chlorine (12.97 g, 0.183 mol) was passed into the mixed suspension during 60 minutes, and the reaction mixture was mixed another 0.5 h at 25° C.

Condensation

A solution of 2-benzthiazolylsulfenyl chloride was cooled down to 0° C., and 45 g (0.61 mol) of concentrated tert-butylamine were added to it from a dropping funnel within 100 minutes at 0° C. After the amine adding had been completed, the mixture was mixed for 1.5 h under stirring and then the cooling was removed within 0.5 h.

Extraction of tert-butylamine

From the reaction mixture containing TBSI alkylamine hydrochloride and free tert-butylamine were isolated by multiple extraction with water and gravitational discharge of the aqueous phases.

Isolation of the Crude Product

To the extracted reaction mixture 800 ml of water were added and the solvent was azeotropically distilled off at a reduced pressure in such a way, that the temperature in the apparatus did not exceed 50° C. The crude product (TBSI)

was obtained from the aqueous phase by filtration. After completion of drying 71.7 g, i.e. 102% of the theoretical yield, of the crude product containing up to 90% of the active substance, was obtained; already this crude (not refined) product can be used as a rubber accelerator.

Crude Product Refining

The wet filter cake was physically refined during 1 h by elutriation in a 7-fold amount of technical isopropanol at ambient temperature. After filtration and drying 62.36 g of the refined product was obtained having a 96.9% purity according to HPLC, the yield being 88.7% of the theoretical value.

Example 2

Chlorination of disulfide, condensation with tert-butylamine and extraction of tert-butylamine were performed using the procedure from Example 1.

Crude Product Isolation

To the extracted reaction mixture 800 ml of water and 82 g of 18% aqueous NaOH were added. Chemical refining directed at decomposition of the disulfide which had not reacted took place during 2 h of azeotropic distillation of toluene at a reduced pressure and under stirring at a temperature under 50° C. The crude product was filtered off from the aqueous phase and washed with water.

Crude Product Refining

The filter cake obtained was physically refined during 1 h by elutriation in a 3-fold amount of acetone at ambient temperature. After filtration and drying 60.74 g of the refined product were obtained having a 98.3% purity according to HPLC (yield 86.4% of the theoretical value).

Example 3

Suspension of the crude TBSI in water (obtained after azeotropic distillation of toluene) was prepared by the procedure, given in Example 2.

To the crude product in water, a half amount of toluene, referred to the weight of the crude product, was added and the mixture was physically refined by mixing for 1 h at 50° C. After cooling down, filtration and drying 60.7 g of the refined product were obtained having 96.97% purity according to HPLC (yield 86.3% of theoretical value).

Example 4

Suspension of the crude TBSI in water (obtained after azeotropic distillation of toluene) was prepared by the procedure, given in Example 2.

Double amount of cyclohexane, referred to the weight of the crude product, was added to it and the mixture was physically refined by mixing for 1 h at 50° C. After cooling down, filtration and drying 63.7 g of the refined product were obtained having 96.33% purity according to HPLC (yield 90.6% of the theoretical value).

Example 5

Preparation of
N-tert-butyl-2-benzthiazolylsulfeneimide (TBSI) in cyclohexane

Chlorination 20 g (0.058 mol) of 2,2'-dibenzthiazolyldisulfide (commercially available Altax containing 96.51% of the active substance according to HPLC) was mixed with 320 ml of cyclohexane in a 500 ml three-necked flask and 30 ml of the solvent were distilled off. 4.3 g (0.061 mol) of chlorine were added within 60 minutes in a temperature range of 40 to 45° C., the mixture was heated to 75° C., and blown through with nitrogen.

Condensation

The reaction mixture was cooled down to 10° C., 23.4 g (0.32 mol) of tert-butylamine were added during 120 minutes, and it was stirred 60 minutes at a reaction temperature.

Refining

After water and NaOH solution had been added, 60% of the solvent were distilled off from the reaction mixture at a reduced pressure and at a temperature not greater than 50° C. After cooling down, filtration and washing with water 19.6 g of the product were obtained having a 97% purity according to HPLC (yield 83.8% of the theoretical value).

Example 6

Chlorination of disulfide and condensation with tert-butylamine were the same as in Example 5.

Refining

After the condensation had been completed, 150 ml of water were added to the flask and the aqueous solution of amine chloride was separated. The organic phase in the flask was washed with 50 ml of water (or diluted acid) two more times and finally 200 ml of water were added and the organic solvent was distilled off completely at a reduced pressure. The crude product was filtered off and refined by mixing for 60 minutes in a 3-fold amount of acetone. After filtration 19.45 g of the product (yield 83%) having 97.6% purity according to HPLC were obtained.

Example 7

Preparation of
N-cyclohexyl-2-benzthiazolylsulfeneimide (CBSI) in cyclohexane

Chlorination of the disulfide was the same as in Example 5.

Condensation

The reaction mixture was cooled down to 10° C., 31.7 g (0.32 mol) of cyclohexylamine were added during 120 minutes, and it was stirred 60 minutes at a reaction temperature.

Refining of the reaction mixture and product isolation were the same as in Example 5.

After drying the filter cake 17.9 g of the product having 98.5% purity according to HPLC (72% of the theoretical yield) were obtained.

Example 8

Preparation of TBSI in a Reactor with a Multiple Propeller Mixer on a Common Shaft Chlorination Benzthiazolylsulfenyl chloride was prepared from 700 kg of 98% commercially available Altax (2.063 kmol) in 8750 l of a solvent and 150 kg chlorine.

Condensation

The solution of 2-benzthiazolylsulfenyl chloride was poured into the vessel (1) of a reactor (FIG. 1) with a lid (2), equipped with propeller mixers (4) on a common shaft (3). It was cooled down to 5° C. and within 120 minutes 604 kg (8.25 kmol) of concentrated tert-butylamine were dosed to it from a volumetric flask at a temperature lower than 15° C. After the amine dosing had been completed, the mixture was mixed for 1 h with cooling (the reactor was equipped with a cooling box) and another hour without cooling.

Crude Product Isolation

After extraction with water water was added to the solution of crude TBSI in an organic solvent and the solvent was distilled off azeotropically at a reduced pressure in such a way, that the temperature in the apparatus did not exceed 50° C. The crude product was obtained from the aqueous phase by filtration. It contained 89% of the active substance (after drying).

Crude Product Refining

The filter cake from the previous filtration was refined during 1 h by elutriation in 5800 l of technical azeotropic isopropanol at ambient temperature. After filtration and drying 725 kg of the refined product was obtained having a 99% purity according to HPLC, the yield being 87.06% of the theoretical value.

What is claimed is:

1. A method for the production of N-alkyl-2-benzthiazolyl-sulfeneimides of the formula I

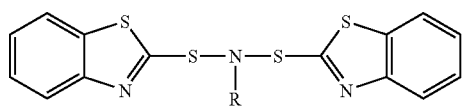

where R is selected from the group consisting of a $C_1$ to $C_{12}$ unbranched or branched alkyl and a $C_3$ to $C_9$ cycloalkyl group, the method comprising reacting a 2-benzthiazolylsulfenyl chloride with an excess of a corresponding alkylamine in an inert solvent reaction medium, wherein the reaction of the sulfenyl chloride with the corresponding alkylamine is performed at a temperature of from +5 to +15° C. using a 10 to 100% excess of the alkylamine compared with a theoretical amount, removing moisture of equipment, solvent, and raw material by distilling off a part of the solvent by azeotropic distillation at an atmospheric or reduced pressure, and removing disulfide which has not reacted by adding aqueous sodium hydroxide at a temperature of 20 to 50° C., while separating the sulfeneimide by filtration.

2. A method according to claim 1, wherein the reaction of the sulfenyl chloride with the corresponding alkylamine is performed with an excess of 3.5 to 4 equivalents of amine per 2 equivalents of sulfenyl chloride.

3. A method according to claim 1, wherein alkylammonium chloride and alkylamine are isolated from the reaction mixture by extraction with water or diluted acid and subsequent separation of phases.

4. A method according to claim 1, wherein the solvent is removed by distilling it off using azeotropic distillation in the presence of water, at a reduced pressure and at a temperature no greater than 50° C.

5. A method according to claim 1, additionally comprising purification of crude product N-alkyl-2-benzthiazoylsulfeneimide by elutriating crude product for 0.5 to 2 hours at a temperature of 10 to 50° C. in a suitable polar organic solvent or in its azeotropic mixture with water, and subsequently separating the sulfeneimide by filtration.

6. A method according to claim 1, additionally comprising purification of crude product N-alkyl-2-benzthiazoylsulfeneimide by mixing an aqueous suspension of the crude product with a suitable nonpolar organic solvent or with a mixture of such organic solvents, and mixing the resulting mixture for 0.5 to 2 hours at a temperature of 10 to 50° C. and subsequently separating the sulfeneimide by filtration.

7. A method according to claim 2, wherein alkylammonium chloride and alkylamine are isolated from the reaction mixture by extraction with water or diluted acid and subsequent separation of the phases.

8. A method according to claim 2, wherein the solvent is removed by distilling it off using azetropic distillation in the presence of water, at a reduced pressure and at a temperature no greater than 50° C.

9. A method according to claim 3, wherein the solvent is removed by distilling it off using azetropic distillation in the presence of water, at a reduced pressure and at a temperature no greater than 50° C.

10. A method according to claim 2, additionally comprising purification of crude product N-alkyl-2-benzthiazoyl-sulfenemide by elutriating crude product for 0.5 to 2 hours at a temperature of 10 to 50° C. in a suitable polar organic solvent or in its azetropic mixture with water, and subsequently separating the sulfeneimide by filtration.

11. A method according to claim 3, additionally comprising purification of crude product N-alkyl-2-benzthiazoyl-sulfenemide by elutriating crude product for 0.5 to 2 hours at a temperature of 10 to 50° C. in a suitable polar organic solvent or in its azetropic mixture with water, and subsequently separating the sulfeneimide by filtration.

12. A method according to claim 4, additionally comprising purification of crude product N-alkyl-2-benzthiazoyl-sulfenemide by elutriating crude product for 0.5 to 2 hours at a temperature of 10 to 50° C. in a suitable polar organic solvent or in its azetropic mixture with water, and subsequently separating the sulfeneimide by filtration.

13. A method according to claim 2, additionally comprising purification of crude product N-alkyl-2-benzthiazoyl-sulfenemide by mixing an aqueous suspension of the crude product with a suitable nonpolar organic solvent or with a mixture of such organic solvents, and mixing the resulting mixture for 0.5 to 2 hours at a temperature of 10 to 50° C. and subsequently separating the sulfeneimide by filtration.

14. A method according to claim 3, additionally comprising purification of crude product N-alkyl-2-benzthiazoyl-sulfenemide by mixing an aqueous suspension of the crude product with a suitable nonpolar organic solvent or with a mixture of such organic solvents, and mixing the resulting mixture for 0.5 to 2 hours at a temperature of 10 to 50° C. and subsequently separating the sulfeneimide by filtration.

15. A according to claim 4, additionally comprising purification of crude product N-alkyl-2-benzthiazoylsulfeneimide by mixing an aqueous suspension of the crude product with a suitable nonpolar organic solvent or with a mixture of such organic solvents, and mixing the resulting mixture for 0.5 to 2 hours at a temperature of 10 to 50° C. and subsequently separating the sulfeneimide by filtration.

* * * * *